United States Patent [19]
Burges et al.

[11] Patent Number: 4,935,353
[45] Date of Patent: Jun. 19, 1990

[54] **PREPARATION OF STRAINS OF *BACILLUS THURINGIENSIS* HAVING AN IMPROVED ACTIVITY AGAINST CERTAIN LEPIDOPTEROUS PESTS AND NOVEL STRAIN PRODUCED THEREBY**

[75] Inventors: Denis H. Burges, Goring-by-Sea; Paul Jarrett, Littlehampton, both of United Kingdom

[73] Assignee: Agricultural Genetics Company, Limited, Cambridge, England

[21] Appl. No.: 784,562

[22] Filed: Oct. 4, 1985

[30] Foreign Application Priority Data

Oct. 9, 1984 [GB] United Kingdom ............... 8425487

[51] Int. Cl.$^5$ .................... C12N 1/20; C12N 1/00; C05F 11/08
[52] U.S. Cl. .................... 435/69.1; 435/252.31; 435/320; 435/172.3; 935/72; 935/11; 71/6
[58] Field of Search ........... 435/172.3, 252.31, 320, 435/832; 530/324; 935/72, 11

[56] References Cited

PUBLICATIONS

Mating Between *Bacillus subtilis* and *Bacillus thuringiensis* and transfer of cloned crystal genes, Klier et al, Mol. Gen Genet. (1983) 191:257–262.
Genetics in Relation to Insect Management, Dulmage, H. T. (1979).
J. Appl. Bacteriol. 1985, 58 (5), 437–48.
Chemical Abstracts, vol. 95, No. 7, 17 Aug. 1981, p. 343, Abstract No. 57938C.
Plasmid 1981, 5 (3), 351–65.
Arch. Microb. (1982) 132(2) pp. 159–162.
Microb. Contr. Pest. Plant Disease 1970–80 (1981) pp. 299–310–also references 2, 3 and 5 cited in EPO.
Mol. Gen. Genet. (1983) 191, pp. 257–262.
Howard T. Dulmage, et al, Journal of Invertebrate Pathology, vol. 15, No. 1, Jan. 1970, Coprecipitation With Lactose as a Means of Recovering . . . .
Howard T. Dulmage, et al, U.S. Department of Agriculture, ARM-S-30/Oct. 1982, *Bacillus Thuringiensis* Cultures Available from the U.S. Department . . . .
Collection De Souches De *Bacillus thuringiensis,* 1983, Du, Centre Collaborateur O.M.S. De Recherches et De References Pour les Bacteries Sporulees . . . .
P. Jarrett, FEMS Microbiology Letters 16 (1983), 55–60, Comparison of Plasmids From Twelve Isolates of *Bacillus thuringiensis* H–Serotype 7.
P. Jarrett, Journal of Applied Bacteriology, 1985, 58, 437–448, Potency Factors in the Delta–Endotoxin of *Bacillus thuringiensis* Var Aizawa and . . . .
H. D. Burges, Bioassay of *Bacillus thuringiensis,* pp. 244–254, Techniques for the Bioassay of *Bacillus thuringiensis* with *Galleria mellonella.*
Christopher C. Payne, Journal of Invertebrate Pathology 38, 71–77 (1981), The Susceptibility of the Pea Moth, *Cydia nigricana,* to Infection by the . . . Rearing Pieris Brassicae L. Larvae on a Semi-Synthetic Diet, No. 4999, Aug. 21, 1965, NAT.

Primary Examiner—Thomas G. Wiseman
Assistant Examiner—Patricia Carson
Attorney, Agent, or Firm—Oblon, Spivak, McClelland, Maier & Neustadt

[57] ABSTRACT

The invention relates to a strain of *Bacillus thuringiensis,* GC 91, a sample of which has been deposited under the accession number NCTC 11821, or a derivative or mutant thereof having entomocidal activity against lepidopterous pests. The invention also relates to a process for producing a strain of *Bacillus thuringiensis* having improved entomocidal properties by combining into a single strain by plasmid transfer the different entomocidal properties of two respective starting strains. The new strains thus produced are useful in entomocidal compositions.

5 Claims, 1 Drawing Sheet

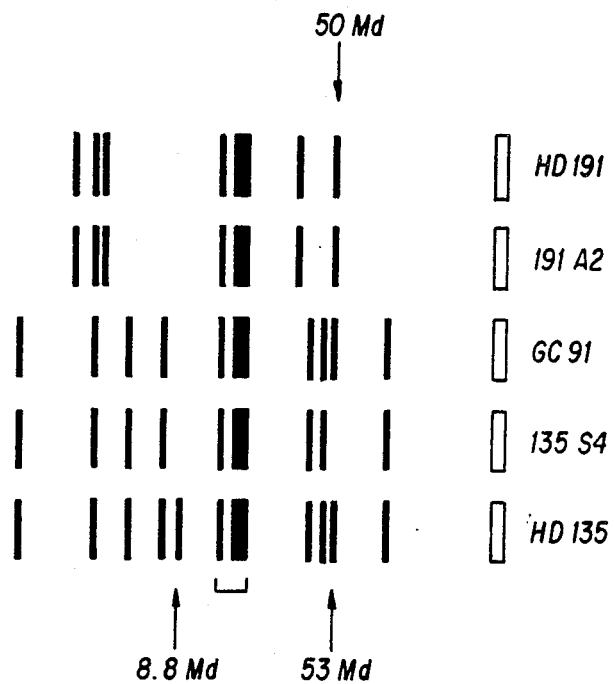

PREPARATION OF STRAINS OF *BACILLUS THURINGIENSIS* HAVING AN IMPROVED ACTIVITY AGAINST CERTAIN LEPIDOPTEROUS PESTS AND NOVEL STRAIN PRODUCED THEREBY

BACKGROUND OF THE INVENTION

1. Field of the Invention

This invention relates to the preparation of new strains of a toxin-producing bacterium having entomocidal activity, a new strain thereby produced and the use of this bacterium to protect plants susceptible to certain pests.

2. Discussion of the Background

More particularly, this invention relates to a new strain of *Bacillus thuringiensis* which has an improved entomocidal activity against certain lepidopterous pests.

Many plants of commercial and/or domestic importance are subject to invasion and damage by lepidopterous pests. These pests are found throughout the world and currently their control requires repeated and costly application of the pesticides which are available.

Many crops are susceptible to a number of lepidopterous pests. Among the most significant pests are the cotton leafworm (*Spodoptera littoralis*), the bollworm (*Heliothis armigera*), the tobacco budworm (*Heliothis virescens*), *Plutella maculipennis, Mamestra brassicae* and *Pieris brassicae*.

Broad spectrum pesticides are a useful and valuable tool for crop protection, but the indiscriminate use of broad spectrum chemical insecticides can disrupt many natural control agents. Since most chemical insecticides are relatively non-selective, they may destroy non-target organisms, including beneficial predators and parasites of destructive pests. Some insects also develop resistance to chemical insecticides, which often make them uncontrollable by these insecticides and may permit minor pests to become major ones.

The introduction of selective microbial insecticides using naturally occurring bacteria as the active and host-specific ingredient has helped to overcome many of these problems.

An example of a microbial insecticide is *Bacillus thuringiensis*, a number of strains of which are commercially available and are currently exploited for their unique insecticidal activity when eaten by susceptible larvae, particularly those of the insect order Lepidoptera.

These strains may be employed without ill effect on beneficial insects. *Bacillus thuringiensis* fits well into current agricultural theories which support the use of naturally occurring organisms to suppress harmful insects. It is a widely distributed, rod-shaped, spore forming, aerobic, gram positive micro-organism and is characterised by producing, during the sporulation cycle, one or more proteinaceous parasporal crystals; its pathogenicity for lepidopterous larvae; its ability to use citrate as its sole source of carbon; and the exceptionally high phosphate content of its spore.

*Bacillus thuringiensis* is a common inhabitant of the environment and is capable of growth in certain types of soils. It has no known adverse effect on life forms such as man, pets, birds, fish, earthworms, most beneficial insects or plants. Its pathogenicity to sensitive insects is essentially due to the presence of a parasporal crystal, which may represent 30 to 40% of the dry weight of the cell at the time of sporulation.

*Bacillus thuringiensis* is active only when ingested. Some hours after ingestion has occurred lepidopterous pests cease to feed and damage to the plant is stopped. Most species die after approximately 24 to 72 hours from toxaemia due to the crystal toxins. This is sometimes accompanied by septicaemia as a result of the presence of the spore.

Thus, the principal effect is due to the crystal which acts only after its dissolution in the intestines of the larvae.

The activation of the crystal is caused by a combination of alkaline pH and proteolytic enzymes in the gut contents. The reaction is dependent on the high gut pH of lepidopterous larvae (pH >7), which allows the release of the toxic components of the crystal. These toxins break down the mid-gut wall causing feeding to stop.

The growth of bacteria thus released into the abdominal cavity results in septicaemia which also may play a part in the death of the insect.

It is clear that the use of *Bacillus thuringiensis* as an insecticide provides an effective and environmentally acceptable method of dealing with lepidopterous pests.

For this reason new strains having improved insecticidal activity, either in terms of greater toxicity for given species or in terms of a broader spectrum of activity, are currently being sought. However, the combination of high toxicity and broad spectrum of activity has in practice been very difficult to achieve.

SUMMARY OF THE INVENTION

It has now been found that a new strain of *Bacillus thuringiensis*, GC91, has an improved entomocidal activity against certain lepidopterous pest species, which has effectively broadened the spectrum of activity.

Accordingly, the present invention provides a novel strain of *Bacillus thuringiensis*, GC91, a sample of which has been deposited at the National Collection of Type Cultures (NCTC), Central Public Health Laboratory, Colindale Avenue, London NW9 5HT, under the accession number: NCTC 11821, deposited on Sept. 7, 1984, or a derivative or mutant thereof having entomocidal activity against lepidopterous pests.

This new strain effectively combines the potential entomocidal activities of two strains of *Bacillus thuringiensis*, one of which is an asporogenic mutant and so does not exhibit entomocidal activity although it contains the genetic material which would enable it to do so if it did produce spores or crystals. Thus, the surprising potency of the new strain, GC91, cannot be achieved by the use of a mere admixture of the two mutant strains.

DETAILED DESCRIPTION OF THE PREFERRED EMBODIMENTS

The novel strain has an improved entomocidal activity against lepidopterous pests in the genera *Galleria, Mamestra, Heliothis, Spodoptera* and *Pieris*.

The invention also provides a process for producing a strain of *Bacillus thuringiensis* having improved entomocidal properties by combining into a single strain the different entomocidal properties of two respective starting strains, which comprises:

(a) selecting from a first starting strain a mutant characterised by loss of a plasmid coding for a polypeptide which forms part of the crystal protein; and (b) transferring a plasmid which codes for delta-endotoxin crystal synthesis from a second starting strain (donor) or mutant thereof into the mutant (recipient) produced in step (a), to thereby produce the desired new strain.

Preferably, there is first selected from the second starting strain an asporogenic mutant having substantially the same plasmid profile as that of the second starting strain. The plasmid is then transferred from the asporogenic mutant into the recipient mutant produced in step (a).

Preferably, the first starting strain is strain HD 135 and the mutant produced in step (a) is strain 135-S4 (NCTC 11822).

Preferably, the second starting strain is strain HD 191 and the asporogenic mutant is strain 191-A2 (NCTC 11823).

The invention further provides a process for producing *Bacillus thuringiensis* GC 91 (NCTC 11821), which comprises transferring from *Bacillus thuringiensis* strain 191-A2 (NCTC 11823) into *Bacillus thuringiensis* strain 135-S4 (NCTC 11822) a plasmid which codes for delta-endotoxin crystal synthesis in strain 191-A2.

In an embodiment of this process, strains 191-A2 and 135-S4 are grown together in mixed culture to effect conjugation-like plasmid transfer, the mixed culture is diluted and transferred to a solid medium to obtain single colonies, colonies of strain GC 91 are selected by the increased size of the parasporal crystal and the strain GC 91 is cultured therefrom.

The invention also provides an entomocidal substance derived from *Bacillus thuringiensis* strain GC 91 (NCTC 11821), or from a derivative or mutant thereof, or from a strain produced according to a process as defined above. In one embodiment the entomocidal substance is a spore-crystal complex.

The invention further provides an entomocidal composition comprising *Bacillus thuringiensis* strain GC 91 (NCTC 11821), or a derivative or mutant thereof, or an entomocidal substance as defined above, together with an agricultural adjuvant such as a carrier, diluent, surfactant or application-promoting adjuvant. The composition may also contain a further biologically active compound selected from fertilisers, micronutrient donors, plant growth preparations, herbicides, insecticides, fungicides, bactericides, nematicides and molluscicides and mixtures thereof. The composition may comprise from 0.1 to 99% by weight of *Bacillus thuringiensis* GC 91 or the derivative or mutant thereof, or the entomocidal substance; from 1 to 99.9% by weight of a solid or liquid adjuvant, and from 0 to 25% by weight of a surfactant.

The invention in addition provides a method of combatting lepidopterous pests which comprises applying to the pests or to their environment an entomocidally effective amount of *Bacillus thuringiensis* strain GC 91 (NCTC 11821), or a derivative or mutant thereof, or an entomocidal substance as defined above, or a composition containing said strain, derivative, mutant or substance.

The strain of *Bacillus thuringiensis*, GC91, or the composition containing it, may be administered to the plants or crops to be protected together with certain other insecticides or chemicals without loss of potency.

It is compatible with most other commonly used agricultural spray materials but should not be used in extremely alkaline spray solutions.

It may be administered as a dust, a suspension, a wettable powder or in any other material form suitable for agricultural application.

During production by fermentation, after normal growth of *Bacillus thuringiensis*, the mother cells lyse and release the spores and crystals into the growth medium. The spores and crystals may be harvested by centrifugation or filtration, spray drying, vacuum drying, or a method of precipitation, such as the lactose co-precipitation technique as reported by Dulmage et al. (Journal of Invertebrate Pathology, 15, 15–20, 1970). The resulting spore-crystal complex is stable for long periods and can be formulated into a product suitable for application to crops.

A method for preparing an insecticidal composition according to the invention comprises culturing the *Bacillus thuringiensis* strain GC 91 by:
(A) maintaining this strain in lyophilized ampules,
(B) inoculating with this strain on agar slopes,
(C) incubating these slopes for 1 to 5 days at 20° to 40° C., preferably 25° to 33° C.,
(D) inoculating from these slopes into shaken flasks containing an aqueous culture medium,
(E) shaking this container at a temperature of 20° to 40° C., preferably 30° C., for 1 to 5, preferably 1 to 2 days and optionally repeating this vegetative growth stage at least once in a separate flask,
(F) inoculating in a preculture fermenter an aqueous cultivating medium with the cultures of stage (E),
(G) stirring and aerating the medium containing the inoculate at a temperature of 20° to 40° C., preferably 30° to 35° C., and optionally repeating this preculture fermentation stage at least once in a separate larger container,
(H) introducing 2 to 20 percent by weight of the incubating liquor of stage (G) into a production fermenter containing an aqueous cultivating medium,
(I) stirring and aerating the medium at a temperature of 20° to 40° C., preferably 30° to 35° C.,
(J) harvesting the *Bacillus thuringiensis* GC 91 broth when sporulation and crystal production in the production fermenter reaches a maximum,
(K) the agar and broth in A to D should contain at least one nitrogen source, at least one carbon source, and at least one salt, preferably peptone, glucose and at least one salt. The media in F to J should contain at least one nitrogen source (e.g., peptone, yeast extract, corn steep liquor, soya bean meal, cotton seed meal, fishmeal), at least one carbohydrate source (e.g., glucose, lactose, sucrose, starch or raw material rich in these constituents) and at least one mineral salt. The nitrogen and carbohydrate should be balanced to exhaust as near as possible simultaneously.

The spore-crystal complex or the composition containing it may be administered to the plants or crops to be protected together with certain other insecticides or chemicals without loss of potency.

It is possible to kill the spores in the spore-crystal complex, for example by gamma radiation or some other method which does not damage the crystal, or to avoid producing spores by use of an asporogenous crystaliferous mutant, thereby producing a non-viable product. A non-viable product may be advantageous in certain circumstances where it is desired to prevent the spread of bacteria for aesthetic reasons or to avoid causing disease in beneficial lepidoptera, e.g. silkworms.

However, non-viable products are generally not as active as those containing live spores, and as a further disadvantage there is the increased cost of killing the spores.

The invention furthermore relates to a method of treating plants, which comprises applying an entomocidally effective amount of *B. thuringiensis* GC91, or a composition thereof.

Target crops to be protected within the scope of the present invention comprise e.g. the following species of plants:

cereals (wheat, barley, rye, oats, rice, sorghum and related crops), beet (sugar beet and fodder beet), drupes, pomes and soft fruit (apples, pears, plums, peaches, almonds, cherries, strawberries, rasberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fibre plants (cotton, flax, hemp, jute), citrus fruit (oranges, lemons, grapefruit, mandarins), vegetables (spinach, lettuce, asparagus, cabbages and other brassicae, onions, tomatoes, potatoes, paprika), lauraceae (avocados, carrots, cinnamon, camphor), deciduous trees and conifers (e.g. linden-trees, yew-trees, oak-trees, alders, poplars, birch-trees, firs, larches, pines), or plants such as maize, tobacco, nuts, coffee, sugar cane, tea, vines, hops, bananas and natural rubber plants, as well as ornamentals (including composites). *Bacillus thuringiensis,* GC91, is normally applied in the form of compositions and can be applied to the crop area or plant to be treated, simultaneously or in succession, with further biologically active compounds. These compounds may be both fertilisers or micronutriant donors or other preparations that influence plant growth. They may also be selective herbicides, insecticides, fungicides, bactericides, nematicides, mollusicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, takifiers, binders or fertilisers.

The formulations, i.e. the compositions, preparations or mixtures containing *B. Thuringiensis,* GC 91, as an active ingredient or combinations thereof with other active ingredients, and, where appropriate, a solid or liquid adjuvant, are prepared in known manner e.g. by homogeneously mixing and/or grinding the active ingredients with extenders, e.g. solvents, solid carriers, and in some cases surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the active ingredients to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the forms of alkali metal salts, alkaline earth metal salts or unsubstituted or substituted ammonium salts and generally contain a $C_8$–$C_{22}$ alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactant are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one $C_8-C_{22}$ alkyl radical and, as further substituents, lower unsubstituted or halogenated alkyl, benzyl or hydroxyl-lower alkyl radicals. The salts are preferably in the form of halides, methylsulfates or ethylsulfates, e.g. stearyl-trimethylammonium chloride or benzyldi-(2-chloroethyl)ethylammonium bromide.

The surfactants customarily employed in the art of formulation are described e.g. in "McCutcheon's Detergents and Emulsifiers Annual", MC Publishing Corp. Ridgewood, N.J., 1979; Dr. Helmut Stache, "Tensid Taschenbuch" (Handbook of Surfactants), Carl Hanser Verlag, Munich/Vienna.

The entomocidal compositions usually contain 0.1 to 99%, preferably 0.1 to 95%, of Bacillus thuringiensis, GC91, or combination thereof with other active ingredients, 1 to 99.9% of a solid or liquid adjuvant, and 0 to 25%, preferably 0.1 to 20%, of a surfactant.

Whereas commercial products are preferably formulated as concentrates, the end user will normally employ dilute formulations of substantially lower concentration.

The compositions may also contain further ingredients, such as stabilisers, antifoams, viscosity regulators, binders, tackifiers as well as fertilisers or other active ingredients in order to obtain special effects.

Reference is now made to the accompanying drawing which shows plasmid profiles of wild-type, mutant donor, mutant recipient and recombinant strain GC91. The bracket () indicates the position of the chromosomal DNA.

The new strain of *Bacillus thuringiensis*, GC91, was elaborated from two other *Bacillus thuringiensis* strains using the following experimental protocol described in the Examples.

EXAMPLE 1

Preparation of Strain 135-S4

The starting strain was a wild-type, H-serotype 7, var aizawai strain of *Bacillus thuringiensis*, HD 135 (freely available from Dr. H. T. Dulmage, Cotton Insects Research Laboratory, U.S. Dept. of Agriculture, Brownsville, Tex.). Strain HD 135 is listed in the catalogue entitled "*Bacillus thuringiensis* cultures available from the U.S. Department of Agriculture", Agricultural Reviews and Manuals ARM-S-30/Oct. 1982. It is also listed as available in the catalogue entitled "Collection de Souches de *Bacillus thuringiensis* 1983" of Institute Pasteur, 25 rue de Docteur Roux, 75724 Paris Cedex 15, France (index number 7–28).

Strain HD 135 showed entomocidal activity to *Pieris brassicae, Mamestra brassicae, Heliothis virescens, Heliothis armigera, Galleria mellonella* and *Spodoptera littoralis* (See Table 1 below).

Strain HD 135 was grown in Nutrient Broth (Oxoid Ltd, U.K.) (Composition: Lab-Lemco Powder 1.0 g/l, yeast extract L-20 2.0 g/l, Peptone L-37 5.0 g/l, NaCl 5.0 g/l) for 16 hours at 42° C. The culture was then diluted in 0.8% (W/V) bactopeptone (Difco) and plated onto Nutrient agar (Oxoid Ltd, U.K.) (Composition as Nutrient Broth, but with addition of Agar No. 3 15.0 g/l) to achieve approximately 100 colonies per plate. Incubation was then carried out for 48 hours at 30° C. Individual colonies were microscopically examined and one colony was found to produce parasporal crystals of reduced size. This colony was found to be a mutant strain of HD 135 and was designated 135-S4. Strain 135-S4 has been deposited at NCTC under the accession number NCTC 11822, deposited on 7th Sept. 1984. Analysis of the plasmids in the mutant 135-S4 by the method of Jarret, P. (1983), [FEMS Microbiology Letters 16, pp. 55–60] showed it to be lacking a 53 Md plasmid and an 8.8 Md plasmid which were present in the parent strain (see drawing). Electrophoresis on SDS (sodium dodecyl sulphate) polyacrylamide gels of solubilized crystal protein from the wild type, HD 135, and 135-S4 showed that the parasporal crystals of 135-S4 lacked a polypeptide of Mr 130K. The methods used to purify crystals, dissolve them and run them on SDS polyacrylamide gels are known in the art and described, for example, by P. Jarrett, Journal of Applied Bacteriology 1985, 58, 437–448. Bioassay of strain 135-S4 showed that entomocidal activity was lost to *Pieris brassicae* and *Heliothis virescens* but retained in *Mamestra brassicae, Galleria mellonella, Heliothis armigera* and *Spodoptera littoralis* (Table 1).

Activities of the bacterial strain to *Galleria mellonella* were performed using the artificial food assay method of Burges, H. D. (1976), [Entomologia Experimentalis et Applicata 19, 217–222].

Activities of bacterial strains to *Heliothis armigera, Heliothis virescens, Mamestra brassicae* and *Spodoptera littoralis* were performed by the addition of a series of concentrations of the bacteria to an artificial agar-based diet on which the larvae fed. The diets used are described by Payne, C. C. (1981) [Journal of Invertebrate Pathology 38, 71–77].

For *Pieris brassicae* the semi-synthetic diet of David, W. A. L. and Gardiner, R. O. C. (1965), [Nature, London 207, No. 4999, pp 882–883] was used. All larvae used for bioassay were 6 days old. Mortality was recorded after 6 days with the temperature maintained at 25° C.

The entomocidal activity of strain 135-S4 to a number of lepidopterous pests is shown in Table 1.

EXAMPLE 2

Preparation of Strain 191-A2

A second mutant strain, coded 191-A2, was derived from a wild-type H-serotype kurstaki strain HD 191 (obtained from Dr. H. T. Dulmage, Cotton Insects Research Laboratory, U.S. Dept. of Agriculture, Brownsville, Tex.). Strain HD 191 is listed as available in the catalogues of the U.S. Department of Agriculture and the Institute Pasteur (index number 30–49) referred to in Example 1.

Strain HD 191 was streaked onto the surface of Nutrient agar (composition of media: Lab-Lemco Powder (L-29) 1.0 g/liter, Yeast Extract (L-20) 2.0 g/liter, Peptone (L-37) 5.0 g/liter, sodium chloride 5.0 g/liter, Agar No. 3 15.0 g/liter) and incubated at 42° C. for 48 hours. After incubation, the plates were examined under a dissecting microscope at about 8 times magnification. Many small, raised areas or papillae were observed scattered throughout the streaks, indicating asporogenic colonies. These were picked out and restreaked onto Nutrient agar and incubated at 30° C. for 48 hours. The resulting growth allowed the isolation of a stable, asporogenic mutant strain(designated 191-A2) as a single colony. Strain 191-A2 has been deposited at NCTC under the accession number NCTC 11823, deposited on 7th Sept. 1984.

No difference between the parent and the mutant strain was detected when plasmid profiles of the two were analysed by agarose gel electrophoresis (see drawing). This indicated that the plasmid profile for entomocidal activity was probably the same as that of the spore-producing parent HD 191, i.e. entomocidal activity against *Heliothis armigera, Heliothis virescens* and *Pieris brassicae* (Table 1).

EXAMPLE 3

Preparation of Strain GC 91

Using the conjugation-like plasmid transfer system reported by Gonzalez, J. M. Jr., Brown, B. J. and Carlton, B. C. (1982) [Proc. Natl. Acad. Sci. USA Vol 79, pp 6951–55] with the following variation, the mutant strain 191-A2 was tested to identify which plasmid was responsible for toxin production.

The donor 191-A2 and the recipient strain, an acrystaliferous mutant derived from the *Bacillus thuringiensis* strain HD 1, were grown separately on Brain Heart Infusion agar (Oxoid) plates [ingredients in g/l: Calf Brain Infusion Solids 12.5, Beef Heart Infusion Solids 5.0, Protease Peptone (Oxoid L 46) 10.0, sodium chloride 5.0, dextrose 2.0, sodium phosphate anhyd. 2.5 and Agar No. 3 15.0]. After incubating for 16 hours at 30° C., a loopful of cells from each strain are mixed together on the surface of a Brain Heart Infusion agar plate and incubated for a further 24 hours at 30° C. The resulting growth is then streaked onto Nutrient agar plates (Oxoid) and incubated for 48 hours at 30° C. to allow the recipient to sporulate. A loopful of growth from the nutrient agar plate is then suspended into 10 ml of sterile distilled water and heated at 60° C. for 15 minutes to kill the asporogenous donor 191-A2 (the spore-forming recipient is unharmed). Reversion of the donor 191-A2 to produce heat resistant endospores occurred at frequencies of $>1$ in $10^7$ viable cells after growth on Nutrient agar plates.

After heating, the culture was diluted and plated onto Nutrient agar to obtain individual colonies. After incubation for 48 hours at 30° C., colonies were microscopically examined to look for the presence of delta-endotoxin crystals. The percentage of colonies producing crystals in four separate experiments were 59%, 41%, 22% and 31%. The plasmid profiles from recipients regaining crystal production showed that crystal synthesis was accompanied by the transfer of a 50 Md plasmid from the donor 191-A2. Twenty individual colonies were examined and all contained the 50 Md plasmid. Recipients receiving the 50 Md plasmid from 191-A2 showed the full biological activity of the donor wild-type parent HD 191. The results are shown in Table 2. From this data it was concluded that a 50 Md plasmid coded for delta-endotoxin crystal synthesis in 191-A2.

Using the above method of plasmid transfer and selection of heat-resistant, spore-forming recipients, the 50 Md plasmid from 191-A2 was transferred into the mutant 135-S4. Individual colonies of 135-S4, possibly containing the 50 Md plasmid, colonies were microscopically examined to select for those producing crystals of increased size. The percentage of 135-S4 colonies producing crystals of increased size after plasmid transfer in two separate experiments was 29% and 21%. Plasmid profiles of such colonies showed the presence of a 50 Md plasmid in all (10) large crystal-producing colonies analysed. It was concluded that uptake of the 50 Md plasmid resulted in an increase in the size of the parasporal crystal and concomitant alteration and increase in the entomocidal activity of the mutant 135-S4.

The combined entomocidal activity was improved in respect of the pest species *Spodoptera littoralis, Heliothis armigera, Heliothis virescens, Mamestra brassicae, Galleria mellonella* and *Pieris brassicae.*

Mutant 135-S4 containing the additional 50 Md plasmid was designated as mutant GC91.

The entomocidal activities of strain GC91 and of other strains of *Bacillus thuringiensis* are given in Table 1.

Reference is also made to the accompanying drawing which shows plasmid profiles of the wild-type, mutant donor, mutant recipient and recombinant strain GC91. The bracket (]) indicates the position of the chromosomal DNA.

TABLE 1

| | BIOASSAY DATA | | | | |
|---|---|---|---|---|---|
| | $LC_{50}$ μg bacteria */*g of insect food | | | | |
| Insect species | HD1* | HD191 | HD135 | 135-S4 | GC91 |
| *Galleria mellonella* | 2,600 | 3,500 | 20 | 64 | 18.4 |
| *Heliothis armigera* | 42 | 48 | 228 | 845 | 44 |
| *Heliothis virescens* | 8.6 | 5.8 | 205 | >2000 | 4.8 |
| *Spodoptera littoralis* | 5,780 | 10,000 | 445 | 694 | 330 |
| *Pieris brassicae* | 0.64 | 0.98 | 1.2 | >100 | 0.72 |
| *Mamestra brassicae* | 1,510 | >10,000 | 185 | 282 | 162 |

*HD1 is the bacterial stain used in most commercial *Bacillus thuringiensis* products for control of lepidoterous larvae. It is available, for example, from the US Department of Agriculture and the Institute Pasteur (details given in Example 1)

**Bacteria were cultured and harvested for bioassay according to the method of Dulmage et al (1970) [Journal of Invertebrate Pathology 15, 15–20].

TABLE 2

| | BIOASSAY DATA | | |
|---|---|---|---|
| | $LC_{50}$ μg bacteria /g of insect food | | |
| Insect species | Acrystaliferous HD 1 | HD 191 | Crystal-producing recipient |
| *Galleria mellonella* | >100,000 | 3,750 | 2.940 |
| *Heliothis armigera* | >10,000 | 57.0 | 52.0 |
| *Heliothis virescens* | >10,000 | 6.4 | 6.2 |

Formulation Examples for solid active ingredients of *Bacillus thuringiensis* GC91, or combinations thereof with other active ingredients (throughout, percentages are by weight)

| | (a) | (b) | (c) |
|---|---|---|---|
| 1. Wettable powders | 25% | 50% | 75% |
| *Bacillus thuringiensis*, GC91, | | | |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

*Bacillus thuringiensis*, GC91, is thoroughly mixed with the adjuvants and the mixture is thoroughly ground in a suitable mill, affording wettable powders which can be diluted with water to give suspensions of the desired concentration.

| 2. Emulsifiable concentrate | 10% |
|---|---|
| *Bacillus thuringiensis*, GC91, | |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| | (a) | (b) |
|---|---|---|
| Dusts | 5% | 8% |
| *Bacillus thuringiensis*, GC91, | | |
| talcum | 95% | — |
| kaolin | — | 92% |

Ready for use dusts are obtained by mixing the active ingredient with the carriers, and grinding the mixture in a suitable mill.

| 4. Extruder granulate | 10% |
|---|---|
| *Bacillus thuringiensis*, GC91, | |
| sodium lignosulfonate | 2% |
| carboxymethylcellulose | 1% |
| kaolin | 87% |

The active ingredient or combination is mixed and ground with the adjuvants, and the mixture is subsequently moistened with water. The mixture is extruded, granulated and then dried in a stream of air.

| 5. Coated granulate | 3% |
|---|---|
| *Bacillus thuringiensis*, GC91, | |
| polyethylene glycol (mol. wt. 200) | 3% |
| kaolin | 94% |

The finely ground active ingredient or combination is uniformly applied, in a mixer, to the kaolin moistened with polyethylene glycol. Non-dusty coated granulates are obtained in this manner.

| 6. Suspension Concentrate | 40% |
|---|---|
| *Bacillus thuringiensis*, GC91, | |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or combination is intimately mixed with the adjuvants, giving a suspension concentrate from which suspensions of any desired concentration can be obtained by dilution with water.

The novel strains of *Bacillus thuringiensis* disclosed herein, i.e. GC91, 135-S4 and 191-A2, all have, apart from the exceptions specifically mentioned, the morphological and biochemical characteristics typical of the genus and species. Different varieties can be distinguished by H-serotyping (based on flagellar or H-antigens) as described by H. de Barjac (1981), [Chapter 3 in Microbial Control of Pests and Plant Diseases 1970–1980, Ed. H. D. Burges, Academic Press, 1981].

The following biochemical characteristics of NCTC 11821 (=GC91), NCTC 11822 (=135-S4), and NCTC 11823 (=191-A2) have been tested:

| | 11821 | 11822 | 11823 |
|---|---|---|---|
| Gram reaction | + | + | + |
| Motility (Hanging drop) | + | + | + |
| Gaseous conditions | Aerobe | Aerobe | Aerobe |
| Growth on Nutrient Agar at | | | |
| at 22° C. | + | + | + |
| 37° C. | + | + | + |
| 42° C. | + | + | + |
| 60° C. | — | NT | — |
| Koser's citrate | — | — | — |
| Indole | — | — | — |
| Methyl Red | + | + | + |
| Voges-Proskauer | + | + | + |
| Hydrogen sulphide production | — | — | — |
| Nitrates reduced | + | + | + |
| Nitrites reduced | — | — | — |
| Catalase | + | + | + |
| Gelatin liquefied | + | NT | + |
| Acid produced from: | | | |
| Glucose | + | + | + |
| Arabinose | — | — | — |
| Xylose | NT | — | NT |
| Lactose | — | — | — |
| Sucrose | — | — | + |
| Maltose | + | + | + |
| Mannitol | — | — | — |
| Dulcitol | — | — | — |
| Sorbitol | — | — | — |
| Salicin | + | + | + |
| Hydrolysis of Starch: | + | + | + |
| Urea | + | + | + |
| Casein | + | + | + |
| Aesculin | NT | — | NT |
| Hugh and Leifson reaction | NIL | NIL | NIL |
| Oxidase | + | + | + |
| Gluconate | — | NT | — |
| Maltonate | — | — | — |
| Phenylalanine | — | NT | — |
| Decarboxylases: | | | |
| Arginine | + | + | + |
| lysine | — | — | — |
| ornithine | — | — | — |
| Growth on MacConkey | + | NT | + |

(NT = Not Tested)

We claim:

1. A strain of *Bacillus thuringiensis*, GC91, a sample of which has been deposited under the accession number NCTC 11821, or a derivative or mutant thereof having entomocidal activity against lepidopterous pests.

2. A process for producing *Bacillus thuringiensis* GC 91, (NCTC 11821), which comprises transferring from *Bacillus thuringiensis* strain 191-A2 (NCTC 11823) into *Bacillus thuringiensis* strain 135-S4 (NCTC 11822) a plasmid which codes for delta-endotoxin crystal synthesis in strain 191-A2.

3. A process according to claim 2, wherein stains 191-A2 and 135-S4 are grown together in mixed culture to effect conjugation-like plasmid transfer, the mixed culture is diluted and transferred to a solid medium to obtain single colonies, colonies of strain GC 91 are selected by the increased size of the parasporal crystal and the strain GC 91 is cultured therefrom.

4. An entomocidal substance derived from *Bacillus thuringiensis* strain GC 91 (NCTC 11821), of claim 1, or from a derivative or mutant thereof.

5. An entomocidal substance according to claim 4, which is a spore-crystal complex.

* * * * *